United States Patent [19]

Stone

[11] Patent Number: 5,039,618
[45] Date of Patent: Aug. 13, 1991

[54] TEST SWAB CARTRIDGE TYPE DEVICE AND METHOD FOR DETECTING LEAD AND CADMIUM

[75] Inventor: Marcia J. Stone, Wellesley, Mass.

[73] Assignee: Hybrivet Systems, Inc., Framingham, Mass.

[21] Appl. No.: 449,488

[22] PCT Filed: Feb. 2, 1990

[86] PCT No.: PCT/US90/00527

§ 371 Date: May 7, 1990

§ 102(e) Date: May 7, 1990

Related U.S. Application Data

[63] Continuation-in-part of Ser. No. 305,221, Feb. 2, 1989, abandoned.

[51] Int. Cl.⁵ .................... G01N 21/78; G01N 33/20
[52] U.S. Cl. ......................... 436/77; 422/56; 422/58; 422/61; 436/81; 436/169
[58] Field of Search .................. 422/56–58, 422/61; 436/77, 81, 169; 435/294–296; 128/759

[56] References Cited

U.S. PATENT DOCUMENTS

| | | | |
|---|---|---|---|
| 3,446,596 | 5/1969 | Salivar et al. | 422/58 X |
| 3,509,872 | 5/1970 | Truhan | 422/58 X |
| 4,094,967 | 6/1978 | Gilbert | |
| 4,707,450 | 11/1987 | Nason | 422/61 X |
| 4,770,853 | 9/1988 | Bernstein | |
| 4,824,789 | 4/1989 | Yafuso et al. | |
| 4,873,197 | 10/1989 | Gould | 436/77 |

FOREIGN PATENT DOCUMENTS 3618842 12/1987 Fed. Rep. of Germany ........ 436/77

OTHER PUBLICATIONS

P. Elving et al, "Chemical Analysis", 1985, pp. 45–49, 112–113.
Allied Fisher Scientic, "Fisher 86", pp. 496–497, (1985).

*Primary Examiner*—Robert J. Hill, Jr.
*Attorney, Agent, or Firm*—Burns, Doane, Swecker & Mathis

[57] ABSTRACT

A swab is impregnated with a test reagent such that a test for a specific substance can be effected by rubbing the impregnated swab over the surface to be tested and then viewing the swab for a reagent reaction. A method for testing for a metal includes impregnating a swab with a reagent, such as, for example, a rhodizonate dye reagent when testing for lead, and rubbing the swab over a surface suspected of containing the metal. If a metal is present in the surface, a reaction with the metal produces an easily detectable color on the swab tip.

20 Claims, 1 Drawing Sheet

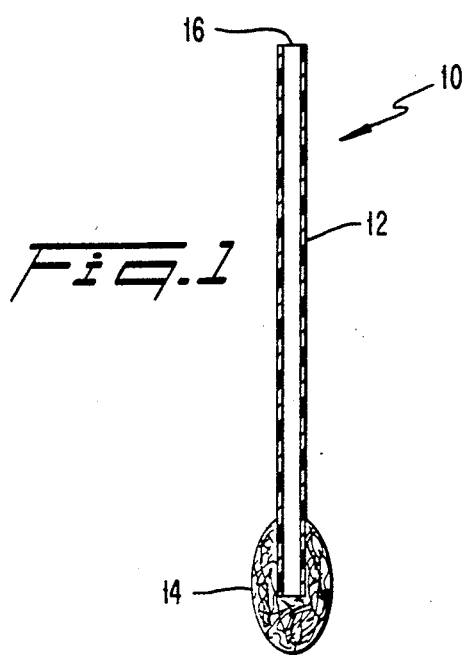
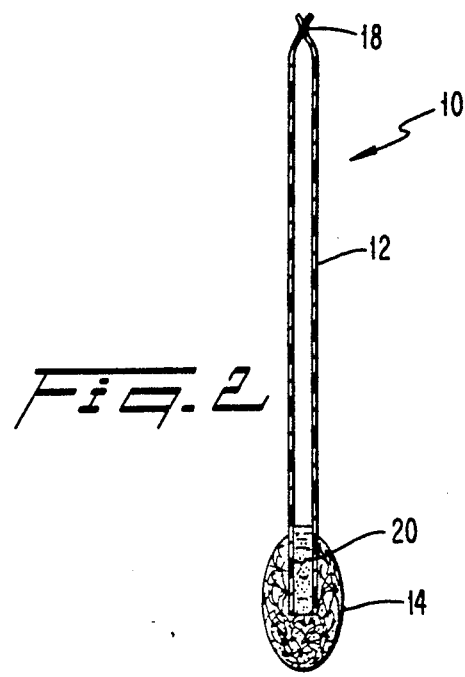
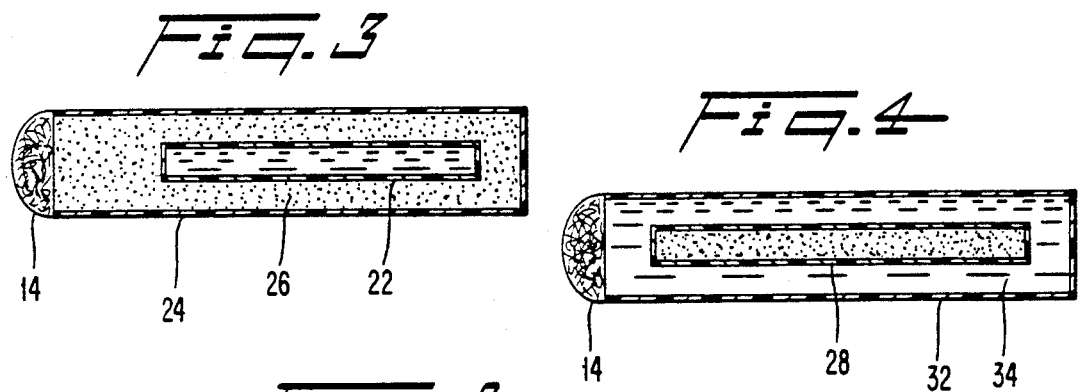
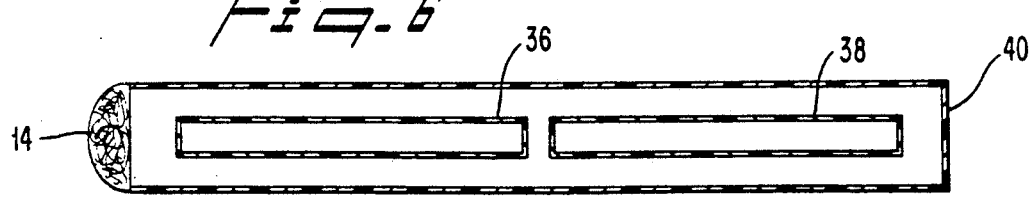

TEST SWAB CARTRIDGE TYPE DEVICE AND METHOD FOR DETECTING LEAD AND CADMIUM

CROSS-REFERENCE TO RELATED APPLICATIONS

This application is a continuation-in-part of application Ser. No. 07/305,221, filed Feb. 2, 1989, now abandoned.

TECHNICAL FIELD

The present invention relates to a swab and a method of using the swab in a test for certain chemical elements, and more particularly, the present invention relates to a swab for retaining test reagents, a method of using the same in a test for metals or other specific elements or compounds, and a method of making the same.

BACKGROUND OF THE INVENTION

Contamination of the environment has been increasing steadily for years as the use of metals, chemicals, pesticides, and bacterial organisms has increased. Even though the toxicity of various metals has been known for centuries, it is only recently that there has been a serious increase in interest in minimizing human exposure to such metals. Current public awareness of such pollutants and their associated hazards has created a consumer demand for products that are capable of determining the presence of unwanted and potentially dangerous materials.

Some of the more toxic metals include lead, cadmium, mercury, barium, chromium and beryllium. Lead, in particular, has been subject to much attention due to its presence in articles or paints commonly found in the home. See, for example, "A Simple Direct Estimation of Ultramicroquantities of Lead in Drinking Water Using Sodium Rhodizonate" by E. Jungreis and M. Nechama, *Microchemical Journal*, vol. 34, pp. 219–221 (1986); U.K. Patent Application No. 2 025 047 A; "A Simplified Method for Detection of Lead Contamination of Soil" by J. Preer and G. Murchison, Jr., *Environmental Pollution* (Series B), vol. 12, pp. 1–13; and "A Spot Test for Detection of Lead in Paint" by J. Sayre and D. Wilson, *J. Pediatrics.* vol. 46, pp. 783–785 (1970).

As the titles of some of the prior art publications indicate, there is a recognized need in the industry for a simple or simplified test or method for determining the presence of lead. However, as will become apparent from the remaining descriptions of the prior art, prior to the present invention, an effective and simple test for lead had not been developed.

In a popular prior art method of detecting lead in paint, sodium sulfide ($Na_2S$) is reacted with lead to form lead sulfide (PbS), a black precipitate. The presence of lead is thus confirmed by the appearance of the black precipitate, lead sulfide. This method has several disadvantages: (1) the sodium sulfide is potentially toxic, especially to young children; (2) the black precipitate is difficult to see on dark surfaces; (3) the sodium sulfide releases volatile hydrogen sulfide ($H_2S$), which has a noxious odor; and (4) the reagents react with many cations to form black precipitates and thus tends to give false readings on many metallic surfaces.

Another common analytical reagent is a metal complexing agent, rhodizonic acid. For over forty years, rhodizonic acid and salts thereof have been used as analytical reagents to detect heavy metals, including lead, in both qualitative and quantitative analyses. The methodology for using rhodizonate dye is based on two types of tests:

(1) a quantitative determination of heavy metals in solutions using a spectrophotometer to obtain quantitative information; and
(2) qualitative determinations which use filter papers impregnated with the reagent.

In addition, semi-quantitative information can be derived from the use of columns packed with silica gel impregnated with rhodizonate dye. See U.K. Patent Application No. 2 025 047 A.

The Macherey-Nagel Company (Düren, Federal Republic of Germany) manufactures a test paper for the determination of lead under the trademark PLUMBTESMO. The PLUMBTESMO strips comprise a heavy filter paper with a reagent impregnated therein. To test for lead in a solution, a strip is dipped into the solution, and observed for a color change that indicates the presence of lead. The PLUMBTESMO strips can also be used to detect lead deposits in motor vehicle tailpipes.

The instruction sheet that is distributed with the PLUMBTESMO strips indicates that the PLUMBTESMO strips may be used to detect the presence of lead on a degreased surface. However, the instruction sheet impliedly recognizes that the PLUMBTESMO strips are not entirely satisfactory for testing for the presence of lead on a surface. Specifically, the instruction sheet indicates that the PLUMBTESMO strip may have to be held firmly against a test surface for as long as fifteen minutes before an indication of lead develops. Clearly, for nonprofessional, household use, a test strip that must be held firmly for fifteen minutes is entirely unsatisfactory in that many users will become impatient after only a few minutes and will discontinue the application of the PLUMBTESMO strip against the test surface. That type of usage may, of course, result in dangerous false readings, leaving the user with the erroneous impression that lead is not present when in fact lead may be present.

A further disadvantage of the PLUMBTESMO strips is that the test operator must directly handle the test strips, thus being unnecessarily exposed to chemicals. Yet another disadvantage of the PLUMBTESMO strips is that the strips are flat and comparatively stiff, and are thus not readily conformable to curved or otherwise unusually contoured surfaces, such as those that one is likely to encounter on moldings in older houses.

Thus, it should be clear that the lead tests, known prior to the present invention, are not entirely satisfactory.

Although not a test for lead, U.S. Pat. No. 4,707,450 discloses a biological specimen collection and test unit. The teachings of U.S. Pat. No. 4,707,450 are quite different from the present invention. In summary, U.S. Pat. No. 4,707,450 discloses a specimen collection device that utilizes a swab to collect biological specimens for testing after the swab has been removed from the specimen collection location. Since lead and other metals do not readily collect on a swab when rubbed on a metal-containing surface, the disclosed swab is not useful for testing for metals. This is especially true because the success of the disclosed swab depends upon the removal of a specimen from the collection site for subsequent testing. Because metals will not usually collect on the swab, the swab will not work well for metals testing.

Thus, there is a need in the art for a test or method for determining the presence of toxic metals, such as lead and cadmium. While lead toxicity is better known, cadmium is toxic by inhalation of dust or fume and is a carcinogen. Cadmium plating of food and beverage containers has led to outbreaks of gastroenteritis or food poisoning. Other metals are just as toxic. Thus, a simple test for metals and other toxic substances would serve to protect consumers from the toxic effects caused thereby.

SUMMARY OF THE INVENTION

Briefly described, the present invention relates to a swab that is impregnated with a test reagent such that a test for a specific substance can be effected by rubbing the impregnated swab over the surface to be tested and then viewing the swab for a reagent reaction. The present invention also relates to a method for testing for a metal that includes impregnating a swab with a reagent, and rubbing the swab over a surface suspected of containing the metal. If the metal is present in the surface, a reaction with the metal produces an easily detectable color on the swab tip. The present invention also relates to a method of making a swab impregnated with a test reagent.

BRIEF DESCRIPTION OF THE DRAWINGS

The present invention may more easily be understood by reference to the drawings, wherein:

FIG. 1 is a view in cross section of a swab according to the present invention prior to the insertion of a reagent.

FIG. 2 is a view in cross section of a swab according to the present invention with a reagent inserted therein.

FIG. 3 is a view in cross section of a cartridge swab according to the present invention containing a breakable cartridge and loose powder.

FIG. 4 is a view in cross section of a cartridge swab according to the present invention containing buffer and a cartridge containing dye.

FIG. 5 is a view in cross section of a cartridge swab according to the present invention containing two cartridges side by side.

FIG. 6 is a view in cross section of a cartridge swab according to the present invention containing two cartridges end to end.

DETAILED DESCRIPTION OF PREFERRED EMBODIMENTS

The test swabs of the present invention may be used to detect a variety of substances on a variety of surfaces depending on the reagent contained in the swab, including but not limited to, paint, ceramics, dust, soil, plant leaves, solder, bird cages, etc. The test swabs may be used to determine the presence of lead, cadmium, bismuth, mercury, antimony, iron, aluminum, selenium, copper or organophosphates. The present invention preferably will be used to determine the presence of metals in such surfaces. In the most preferred embodiments, the test swabs of the present invention are used to determine the presence of lead or cadmium on surfaces.

The swabs can be made in a variety of formats as shown in the Figures, described below.

Referring now in detail to the drawings, wherein like reference numerals refer to like elements throughout, in the embodiments of FIGS. 1 and 2, a swab is indicated generally by reference numeral 10. The swab 10 includes a stem 12 that is preferably formed from a hollow tube. The stem 12 may be made from glass, plastic, or any other suitable material. If plastic is used, the composition of the plastic is not critical. However, because glass is breakable and because plastic is more easily crimped, plastic is preferable to glass.

In an alternative embodiment of the present invention, a solid stem may be used.

At one end of the stem 12, a ball 14 of absorbent material is affixed. The absorbent material may be comprised of any number of materials, including: cotton fibers, rayon fibers, dacron fibers, monofilament polyester, monofilament nylon, or an open cell structure such as polyurethane foam. Table I lists several commercially available swabs, together with the source or manufacturer of each swab.

TABLE I

| ABSORBENT MATERIAL | APPROXIMATE DIAMETER | STICK MATERIAL | STICK DIAMETER | SOURCE |
|---|---|---|---|---|
| Cotton | 0.25" | Plastic | 3/16" | J&J |
| Cotton | 0.25" | Wood | Solid | CitMed |
| Cotton | 0.50" | Wood | Solid | CitMed |
| Rayon | 0.25" | Plastic | 3/16" | CitMed |
| Rayon | 0.50" | Plastic | 5/16" | CitMed |
| Dacron | 0.25" | Plastic | 3/16" | CitMed |
| Nylon | | | | Coventry |
| Polyester | 0.25" | Plastic | 3/16" | Coventry |
| Polyester/cellulose | | | | Coventry |
| Polyurethane | | | | Coventry |
| Porous Plastic | | | | Plastic Interflo |
| Foam dauber | | | | Metal Super Brush Co. |
| Wool dauber | 0.75" | | | Metal Nat'l Novelty Brush Co. |

For purposes of testing for lead, the preferred reagent dye is rhodizonic acid. Table II lists various dyes that are acceptable, together with the supplier or manufacturer of each.

TABLE II

| DYE | SUPPLIER |
|---|---|
| Rhodizonic acid, potassium salt | Sigma Chemical Company |
| Rhodizonic acid, sodium salt | Sigma Chemical Company |
| Rhodizonic acid, disodium salt | Sigma Chemical Company |
| Rhodizonic acid, disodium salt | Eastman Kodak Company |

No major differences in purity or other analytical criteria were reported for similar salts. The above materials all function well in testing for the presence of lead, as indicated below. An activator solution, described below, typically will be used with the reagent dyes in carrying out embodiments of the present invention.

For purposes of testing for cadmium, the preferred reagent dyes are 4-nitronaphthalene-diazoamino-azobenzene or 1-(4-nitrophenyl)-3-(4-phenylazophenyl)-triazene. The latter dye may be obtained from Aldrich as Cadion.

Other substances may be tested for using the reagents and activating solutions listed in Table III.

TABLE III

| Metal | Dye (Reagent which Reacts with Metal) | Activating Solution | Color |
|---|---|---|---|
| Bi | Cinchonine - KI (1%) | Dilute acid | Orange Red |
| Hg | (1) Diphenylcarbazide (1% in alcohol) | 0.2M HNO$_3$ | Violet |
|  | (2) Cobalt (II) thiocyanate test | Cobalt (II) acetate | Deep blue |
| Sb | (1) Rhodamine B (Tetraethylrhodamine) | Sb$^{+5}$ nitrite | Blue |
|  | (2) Phosphomolybdic acid | Sb$^{+3}$ | Blue |
| Fe | (1) 2,2'-bipyridine or 1,1' phenanthroline | Thioglycolic acid buffer | Red |
|  | (2) 3-(2-pyridyl)-5,6-bis(4-phenylsulfonic acid) | 1,2,4-triazine, sodium salt | Purple |
| Al | (1) Aurin tricarboxylic acid | NaOH | Red |
|  | (2) Quinolizarin | Ammonia, then glacial HONC | Red |
| Se | Pyrrole reagent | 0.5M iron (III) chloride; H$_3$PO$_4$ | Green-Blue |
| Organophosphates | Phosphomolybdic acid formed with sodium molybdate | (1) K$_2$S$_2$O$_8$ + H$_2$SO$_4$ (2) Ascorbic Acid | Blue |
| Cu | (1) Quinolyl reagent (0.2 g/l in amyl alcohol) | 20 g Na acetate 10 g K Na tartrate 3 g hydroxylammonium Cl (all in 100 ml H$_2$O) |  |

TABLE III-continued

| Metal | Dye (Reagent which Reacts with Metal) | Activating Solution | Color |
|---|---|---|---|
|  | (2) Dithiooxamide (1% in acetone) (Rubeanic acid) |  | Dark-Green |

Several granular and particulate solids were tried as diluents or fillers for the dyes to be used in the swabs. While fillers are not required, they are useful to provide bulk to the dye when the dye is a solid so the dye can be placed in the swabs more conveniently since the dye is used in a small amount. No filler is needed when the dye to be used is a liquid. All could be used as a filler for the dyes used in the test method of the present invention, but some exhibited more desirable properties than others. The more granular and less sticky solids are preferable to use with automatic filling equipment, such as a Kinematics Powder Filling Machine, model no. 1700 equipped with a model 3015 filling gun.

Table IV identifies several fillers and their ease of use with automatic filling equipment.

TABLE IV

| FILLER | RECOMMENDATION |
|---|---|
| Alumina, acid | Worked well with the machine and filling gun. |
| Talc | Worked well with the machine and filling gun. |
| Silicic acid | Formed a plug, but worked with the machine and filling gun. |
| Glass beads | Formed a plug, but worked with the machine and filling gun. |
| Polyvinylpyrrolidone | Not recommended for use with the filing equipment. |

The rhodizonate dye is unstable in an aqueous medium. As a result, hygroscopic fillers may retain moisture too avidly and will consequently contribute to inactivation of this dye.

Table V identifies several materials capable of use as a filler for the dye, together with comments concerning the suitability of each material.

TABLE V

| BULKING AGENT | APPEARANCE | COMMENTS |
|---|---|---|
| Alumina |  |  |
| WB-2, basic | Loose, sandy | Mixes well; hygroscopic, fills tube easily. |
| WA-1, acidic | Loose | Mixes well; hygroscopic, fills tube easily. |
| WN-3, neutral | Loose | Mixes well; hygroscopic, fills tube easily. |
| Bentonite | Particulate | Colored powder; unsuitable for use. |
| Cellulose |  |  |
| SigmaCell 20 | Loose | Mixes well; fills tube easily. |
| SigmaCell 50 | Loose | Mixes well; fills tube easily. |
| Florisil | Granular | Mixes poorly with dye; fills tube easily. |
| Fuller's Earth | Large Pieces | Particles too large to use. |
| Fumed Silica | Fluffy | Too fluffy; mixes poorly; hard to use for filling. |
| Glass Beads | Sandy | Mixes with dye poorly; fills tube easily. |
| Gum acacia | Loose | Mixes well; fills tube easily. |
| Mannitol | Clumpy | Hygroscopic, dye mixes well. |
| Polyvinylpyrrolidone (PVP) |  | Granular; mixes poorly; unsuitable for filling machine. |
| Silicic acid | Loose | Dye does not mix well; fills tube easily. |
| Starch |  |  |
| Potato* | Loose | Mixes well; turns dark; does not fill easily. |

TABLE V-continued

| BULKING AGENT | APPEARANCE | COMMENTS |
| --- | --- | --- |
| Wheat | Loose | Mixes well; does not fill tube easily. |
| Talc | Powder | Mixes with dye moderately well; fills tube easily. |
| Zeolite | Fluffy Powder | Turns blue with the dye. |
| Zeolite mixture | Fluffy Powder | Turns blue with the dye. |

*Potato starch is susceptible to oxidation, and turns black on reaction with iodine. Rhodizonate reacts with potato starch as iodine does.

Accordingly, alumina (all types), talc, gum acacia, silicic acid, and mannitol are all suitable materials for use as a diluent with the dye. However, other materials in accordance with the spirit of the present invention may be used.

The swabs 10 are filled through the open end 16 of the stem 12, preferably with automatic filling equipment, such as that described above. Once the desired quantity of dye and filler 20 is inserted into the swab 10, the end 16 of the stem 12 may be crimped as shown at 18 in FIG. 2.

In another embodiment, the swabs are filled with a dye/filler mixture using a Kinematics dispensing machine to fill. Then, the solid filled swabs are shaken on a vibrating table to disperse the solid throughout the swab. A four inch wooden applicator is inserted into the swab to prevent loss of reagent through the open end and a drop of glue from a glue gun then is applied to the end of the unit.

Automatic filling units can be designed by using a metal brace notched with the appropriate size holes to ensure that the swabs remain in a fixed position during an automatic filling operation. A conveyor belt can move these units under a fixed dispensing gun. After the dispensing of the solid reagent, the swabs can be sealed by a variety of automatic procedures including, melting to close, using pressure to close and flattening the plastic handle of the swab.

In various tests, swabs were filled with 20, 30, 40, and 80 mg. of the dye and filler. In such tests, the ratios of filler to dye were varied between 0 and 100:1.

In use, the absorbent ball 14 of the filled swab 10 is wetted with an activator solution. A pH level of between about 2.0 and about 3.0 is preferable for the lead-rhodizonate reaction. For the lead reaction, a buffer generally is used as the activator solution. A pH level of 2.8 for the buffer is optimal for the lead-rhodizonate reaction. The wetted absorbent ball 14 is then rubbed onto a surface suspected of containing lead. If lead is present on the surface, a reaction occurs with the rhodizonate dye, thus causing an easily detectable deep pink color to appear on the absorbent ball 14 of the swab 10. The test is even sensitive enough to detect lead dust on a surface caused by sanding lead-containing paint, even after the surface had been vacuumed and washed with trisodium phosphate detergent.

For the cadmium reaction, the activator solution generally will comprise sodium tartrate, sodium acetate, sodium citrate, potassium hydroxide or a mixture thereof. Additional chelating materials such as EDTA may also be present. The pH preferably used for the cadmium reaction is above about 8, more preferably above 9. The potassium hydroxide may be used to adjust the pH. Bases other than hydroxide, which form insoluble cadmium complexes, such as carbonate, might be used. When testing for cadmium, the area to be tested is rubbed with the swab containing the reagent and activator solution. If the swab becomes pink, cadmium is present.

INTERFERENCES CAUSED BY OTHER CATIONS

Many cations form complexes with rhodizonate. However, the specific conditions for optimal reaction of most cations are different from those required for lead. Only barium and lead form a red or deep pink complex under the conditions defined for the swab tests. The color formed by the reaction with barium is red-brown and thus to a skilled technician is distinguishable from the color formed during the reaction with lead. However, to avoid confusion, the reaction with barium can be distinguished from the reaction with lead with the use of sodium sulfide. A drop of sodium sulfide (7.5%) on top of the developed pink swab changes the swab to black in the presence of lead by forming lead sulfide. The precipitate formed by the reaction between sodium sulfide and barium is not black, i.e., sodium sulfide does not change to black in the presence of barium alone.

The solid fill method, described above with the use of a Kinematics filling machine, is the manufacturing option that is best for preserving the stability of the dye reagent. However, alternative manufacturing protocols are also available.

In an alternative method of preparation of a swab for a lead test, an aqueous solution of 0.01M rhodizonate (dye) is prepared. The rhodizonate solution may be prepared using a tartrate buffer at 2.8 pH. Although that pH level is the preferred level for the lead testing reaction, at that pH level, the rhodizonate dye is unstable and completely degrades in about thirty-six hours. As an alternative, the rhodizonate solution can be prepared using water at pH 5 or 6. At that pH level, complete degradation of the rhodizonate takes about ninety-six hours.

The addition of some organic solvents may enhance the stability of the aqueous rhodizonate solution. For example, 10 to 20% methanol, ethanol, or acetone may be added.

Within one hour of preparation of the solution, swabs are dipped in the solution for thirty seconds to one minute. The swabs are then rapidly frozen in acetone/dry ice, or liquid nitrogen, and dried by lyophilization. The swabs can then be used in the same manner as the swabs that are filled from the inside with a filling machine. The swabs can alternatively be dried under heat, although the temperature must be kept below 80° C.

In another embodiment, the swabs can be pretreated by soaking the absorbent material of the swabs in a tartrate buffer, pH 2.8, or any other buffer with a pH preferably between 2 and 3. The soaked swabs are then dried under heat.

Since other cations might interfere with a test for lead, the swab can also be presoaked in a buffer containing EDTA for about one minute in order to clean other possible interfering cations from the swab prior to the test. The EDTA can be included in the buffer described in the preceding paragraph.

In one preferred embodiment, the swab of the present invention is prepared as a cartridge swab. In this embodiment, a device for testing for a substance or metal on a surface comprises a cartridge, two compartments within the cartridge wherein one compartment contains a reagent that reacts with the metal and the other compartment contains an activating solution, and an absorbent ball of material mounted at one end of the cartridge. The reagent and activating solution are combined and mixed within the cartridge before the device is used. This embodiment can take several forms, some of which are shown in FIGS. 3-6.

The simplest design of the cartridge swab is a system wherein two compartments are used. One compartment contains an activator solution and the other contains a dye. When testing for lead, the activator solution will be the buffer solution described above and the dye will be rhodizonate dye. When testing for cadmium, the activator solution will be sodium tartrate, sodium acetate, sodium citrate, potassium hydroxide or mixtures thereof, and the dye will be 4-nitronaphthalene-diazoamino-azo-benzene or 1-(4-nitrophenyl)-3-(4-phenylazophenyl)triazene. The absorbent ball mounted at one end of the cartridge swab may be attached when the cartridge swab is prepared or it may be attached when the cartridge swab is to be used.

FIG. 3 shows an embodiment of a cartridge swab wherein a breakable cartridge 22 contains a small amount of activator solution. The breakable cartridge 22 is inserted into a plastic holder or cartridge 24 into which dry dye powder 26 plus any additives required for the test desired has been dispensed. The swab tip 14 generally will be placed on the cartridge 24 before the cartridge 24 is filled with dry dye powder 26 and the breakable cartridge 22. When the cartridge swab is to be used, the breakable cartridge 22 is broken and the activator solution mixes with the dye powder and wets the swab tip. The swab tip then can be rubbed over the surface to be tested.

FIG. 4 shows an embodiment of a cartridge swab wherein a small breakable cartridge 28 is prepared containing dry dye powder plus any additives required for the desired test. The cartridge 28 is placed inside another breakable cartridge 32 large enough to hold cartridge 28 and sufficient activating solution 34 to execute the desired test. The breakable cartridge is broken when the test is to be performed and the activating solution mixes with the dye and wets the swab tip which can be rubbed over the surface to be tested.

FIG. 5 shows an embodiment of the cartridge swab wherein two breakable cartridges are used side by side in a larger cartridge. Breakable cartridges 36 and 38 will contain either activating solution or dye. The cartridges are broken together when the test is to be performed and the activating solution mixes with the dye and wets the swab tip which can be rubbed over the surface to be tested.

FIG. 6 shows an embodiment of the cartridge swab wherein two breakable cartridges 36 and 38 are used in an end to end format inside a larger cartridge 40 which has a swab tip 14. The cartridges are broken together when the test is to be performed and the activating solution mixes with the dye and wets the swab tip which can be rubbed over the surface to be tested.

The swab tips on the cartridge swabs can be the same type of swabs described above for use on the stick type swabs.

The cartridges which are used to hold the breakable cartridges containing the reactants for the desired test can be nonbreakable or squeezable containers. For example, a squeezable cartridge similar to a toothpaste tube may be used. The breakable cartridges are placed inside the squeezable cartridge and the end is closed with a fibrous or porous swab tip. The swab tip optionally may have a pointed tip which breaks the cartridges contained within the tube. The squeezable cartridge is squeezed, breaking the cartridges within the squeezable cartridge and mixing the reagents. The reagents wet the swab tip which can then be rubbed over the surface to be tested.

Although a filter paper test is not efficient for testing for lead, as described above, such a test may be used for other metals, such as cadmium. For the filter paper format, filter paper may be soaked in an activator solution or the activator solution can be added later. To conduct the test, the activator soaked filter paper is wetted with water and placed on the test surface for about 1 minute to overnight depending on the level of detection required. A drop of dye solution is placed on the test paper and a color change indicates the presence of the metal to be detected. If the activator solution is not on filter paper, it should be added prior to adding the drop of dye. If the dye solution is stable, it can be prepared in the activator solution format. When testing for cadmium, the activator solution and dye is as stated above.

EXAMPLES

TESTS TO DETERMINE PREFERRED RATIOS OF FILLER TO DYE

Examples I through XIII

In examples I through XIII, swabs were obtained from CitMed having an absorbent ball of 0.50 inch diameter made from rayon fibers. The swab stem was a 3/16 inch hollow plastic tube. Alumina (WA-1, acidic) was used as an inert diluent, and rhodizonate dye, disodium salt (from the Sigma Chemical Company) was used as the dye. The inert diluent was mixed with the dye in the ratios set forth in Table V. Table V also lists the quantity of fill used in the swab, together with the test results.

In performing the above examples, the swabs, after being filled with the above-designated quantities of the above-designated ratios of filler and dye, were wetted with 1.5 ml. of 0.2M tartrate buffer, pH 2.8. The swabs were then rubbed on wood that had been previously painted with 0.5% lead-containing paint. In most instances, a positive reaction was clearly visible within seconds, almost always within less than one minute. A positive reaction is indicated by a deep pink color appearing on the absorbent ball of the swab.

TABLE VI

| RATIO ALUMINA:DYE | FILL(mg) | REACTIVITY |
|---|---|---|
| 100:1 | 40 | All positive |
| 100:1 | 80 | All positive |
| 80:1 | 40 | All positive |
| 80:1 | 80 | All positive |
| 60:1 | 40 | All positive |
| 60:1 | 80 | All positive |
| 40:1 | 30 | All positive |

TABLE VI-continued

| RATIO ALUMINA:DYE | FILL(mg) | REACTIVITY |
| --- | --- | --- |
| 40:1 | 40 | All positive |
| 40:1 | 80 | All positive |
| 20:1 | 40 | All positive |
| 20:1 | 80 | All positive |
| 10:1 | 40 | 50% positive - too much dye |
| 5:1 | 40 | no reaction - too much dye |

Example XIV

A mixture of alumina (acidic) and rhodizonate dye, sodium salt at a ratio of 40:1 was suspended in 0.2M tartrate buffer, pH 2.8. The following swabs: cotton, 6" plastic rod, from CitMed; rayon, 6" plastic rod, from CitMed; and dacron, 6" plastic rod, from CitMed, were individually dipped in the suspension. The dipped swabs were then rubbed on a piece of wood painted with a 0.5% lead-containing paint. The suspension lost activity rapidly, losing its ability to detect lead within one minute. It is interesting to note that the suspension lost activity more rapidly when soaked onto the swab, as in this example, than when the mixture was filled through the center of the swab and then wetted with the buffer.

Example XV

A mixture of alumina (acidic) and rhodizonate dye, sodium salt at a ratio of 20:1 was suspended in 0.2M tartrate buffer, pH 2.8. The following swabs: cotton, 6" plastic rod, from CitMed; rayon, 6" plastic rod, from CitMed; and dacron, 6" plastic rod, from CitMed, were individually dipped in the suspension. The dipped swabs were then rubbed on a piece of wood painted with a 0.5% lead-containing paint. The suspension decayed at a rate slower than the suspension used in example XIV. Activity was still observed after five minutes.

Example XVI

A mixture of mannitol and rhodizonate dye, sodium salt at a ratio of 20:1 was suspended in 0.2M tartrate buffer, pH 2.8. The following swabs: cotton, 6" plastic rod, from CitMed; rayon, 6" plastic rod, from CitMed; and dacron, 6" plastic rod, from CitMed, were individually dipped in the suspension. The dipped swabs were then rubbed on a piece of wood painted with a 0.5% lead-containing paint. The suspension decayed at a rate slower than the suspension used in example XIV. Activity was still observed after five minutes.

TESTS TO DETERMINE SENSITIVITY OF REAGENT

Example XVII

To determine the sensitivity of the test, a contoured wood molding strip was divided into ten different sections. Each section was painted with latex paint that was mixed with a different quantity of lead, ranging from 0.1% to 1.0%. The following diagram illustrates the various ratios used:

0.1% 0.2% 0.3% 0.4% 0.5% 0.6% 0.7% 0.8% 0.9% 1.0%

A swab with a 0.5 inch diameter absorbent ball made from rayon fibers and a 5/16 inch hollow plastic stem was filled with 40 mg. of alumina (WA-1, acidic) and rhodizonate dye, disodium salt (from the Sigma Chemical Company) in a 40:1 ratio. A 1.5 ml. solution of 0.2M tartrate buffer, pH 2.8 was used as the developing agent. Within less than thirty seconds, a deep red color developed on the swab after rubbing the treated swab on the wood section painted with 0.4% lead-containing paint. Similarly treated swabs had equal or better results on all sections of the wood having a higher percentage of lead in the paint.

TESTS TO COMPARE RESULTS OF SWAB WITH RESULTS OF FILTER PAPER

Example XVIII

For comparison with the swab test set forth in example XVII above, a similar test was conducted using Whatman 3 mm. filter paper. A solution was prepared using 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8. The filter paper was dipped into the solution, allowing the solution to completely saturate the filter paper. The saturated filter paper was then promptly rubbed over the wood painted with lead-containing paint.

The filter papers never clearly turned pink even when used on the sections of wood having high concentrations of lead. Hints of pink were occasionally visible at the edges of the filter paper; however, interpretation was very difficult. The wood underneath the filter paper did become pink, but this pink color was only visible on the light colored paint, not on the dark paint. On the contoured wood surfaces it was difficult to make good contact between the filter paper and the contoured surfaces.

Example XIX

A swab with a 0.5 inch diameter absorbent ball made from rayon fibers and a 5/16 inch hollow plastic stem was filled with 40 mg. of alumina (WA-1, acidic) and rhodizonate dye, disodium salt (from the Sigma Chemical Company) in a 40:1 ratio. A 1.5 ml. solution of 0.2M tartrate buffer, pH 2.8 was used as the developing agent, i.e., the swab was prepared exactly as set forth in example XVII, above. This time the swab was rubbed on lead-glazed ceramic dishes. Within less than thirty seconds, the tip of the swab was obviously pink.

Example XX

A solution was prepared using 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8. A piece of Whatman 3 mm. filter paper was dipped into the solution, allowing the solution to completely saturate the filter paper, i.e., the filter paper was prepared in accordance with the method set forth above in example XVIII. The treated filter paper was rubbed on the lead-glazed ceramic dishes used in example XIX. No detectable color was observed on the filter paper after several minutes of contact with the lead-glazed dishes.

Example XXI

Plain untreated swabs having a rayon fiber absorbent ball of 0.5 inch diameter on a 5/16 inch hollow plastic stem were soaked in a solution of 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8, i.e., the same solution used in examples XVIII and XX. When the swabs were then rubbed on the lead-glazed ceramic dishes, a clear positive result was easy to read.

Example XXII

Plain untreated swabs having a rayon fiber absorbent ball of 0.5 inch diameter on a 5/16 inch hollow plastic stem were soaked in a solution of 40 mg. of alumina (WA-1, acidic) and rhodizonate dye, disodium salt (from the Sigma Chemical Company) in a 40:1 ratio and a 1.5 ml. solution of 0.2M tartrate buffer, pH 2.8, i.e., the same solution used in examples XVIII, XX, and XXI. When the swabs were then rubbed on the wood painted with at least 0.4% lead-containing paint, a clear positive result was easy to read.

From the results of examples XVII through XXII, it is clear that the swab is far superior to the filter paper for effecting a test for the presence of lead using rhodizonate dye.

COMPARISON OF DIFFERENT TYPES OF SWABS

Example XXIII

A mixture of alumina (acidic) and rhodizonate dye, sodium salt at a ratio of 40:1 was filled into the following swabs: cotton, 6" plastic rod, from CitMed; rayon, 6" plastic rod, from CitMed; and dacron, 6" plastic rod, from CitMed. About 3/16" to ¼" of material was filled in each swab. The swabs were then wetted with tartrate, sodium salt and rubbed on a wood board painted with a 0.5% lead-containing paint.

There were no notable differences in color intensity among the swabs made of cotton, rayon, or dacron. The dacron and rayon swabs wetted well, whereas the first few drops of buffer beaded on the surface of the cotton. During the rubbing stage, the dacron swab did not hold up as well as the cotton and rayon swabs.

Example XXIV

A mixture of mannitol and rhodizonate dye, sodium salt at a ratio of 20:1 was suspended in 0.2M tartrate buffer, pH 2.8. The following swabs: cotton, 6" plastic rod, from CitMed; rayon, 6" plastic rod, from CitMed; dacron, 6" plastic rod, from CitMed; molded foam from Coventry Mfg. Co.; spun foam from Coventry Mfg. Co.; and 3" cotton tipped swabs from Johnson & Johnson, were individually dipped in the suspension. The dipped swabs were then rubbed on a piece of wood painted with a 0.5% lead-containing paint. The foam materials did not wet well, and little or no color formation was observed on the material or the wood. The cotton, rayon, and dacron swabs had intense color on the fibers. Under a microscope it appeared that the fibers had been dyed. It did not appear as though a precipitate had been formed and trapped by the fibers. However, at high concentrations of lead and dye, some precipitate may form. The precipitate is not necessary in order to detect a reaction.

The size of the absorbent ball on the swab also had little apparent effect on the test results.

Example XXV

A swab with a hollow stem is filled with 30 mg of a mixture of 4-nitronaphthalene-diazoamino-azo-benzene and an inert filler, alumina in ratios as shown in Table VI. The swab tip is wetted with an activator solution containing sodium potassium tartrate, sodium acetate, sodium citrate at pH 8.5. The area to be tested is rubbed with the swab. If cadmium is present, the swab becomes pink.

Example XXVI

One crushable cartridge is filled with 30 mg Cadion, (1-(4-nitrophenyl)-3-(4-phenylazophenyl)triazene) and talc. Another breakable cartridge is filled with 0.5 ml activator solution which is a mixture of sodium tartrate, sodium acetate and sodium hydroxide. The pH of the activator solution is adjusted to be basic at a pH greater than 9.

The two cartridges are placed inside a larger cartridge having a swab tip at one end. When ready to use, the breakable cartridges are broken and the unit is shaken to ensure good mixing. The swab tip is rubbed over the area to be tested and becomes pink if cadmium is present.

Although only preferred embodiments are specifically illustrated and described herein, it will be appreciated that many modifications and variations of the present invention are possible in light of the above teachings and within the purview of the appended claims without departing from the spirit and intended scope of the invention. Specifically, the present invention is not limited to tests for the presence of lead or cadmium.

What is claimed is:

1. A method of testing for a substance on a surface with a reagent that reacts with the substance where the substance is lead or cadmium, comprising the steps of:
   providing a swab stick having a stem and an absorbent ball of material at one end of the stem, wherein the absorbent ball of material is impregnated with the reagent;
   contacting the impregnated absorbent ball of material with the surface; and
   detecting the presence of the substance by inspecting the impregnated ball of material for a reaction between the substance and the reagent.

2. The method of claim 1, wherein the stem of the swab stick is hollow, and the step of impregnating the absorbent ball includes injecting the reagent through the hollow stem into the center of the absorbent ball.

3. The method of claim 1, further comprising the step of wetting the absorbent ball of material with a buffer having a pH level conducive to the reaction.

4. The method of claim 1, wherein the substance tested for is lead.

5. The method of claim 4, wherein the reagent comprises rhodizonate dye.

6. The method of claim 5, wherein the reagent further comprises an inert filler.

7. The method of claim 6, wherein the ratio of filler to rhodizonate dye is within the range of about 20:1 to about 100:1 by weight.

8. The method of claim 4, wherein the absorbent ball of material is soaked with a solution comprised of rhodizonate dye, an inert filler and a buffer.

9. The method of claim 1, wherein the substance tested for is cadmium.

10. The method of claim 9, wherein the reagent comprises 4-nitronaphthalene-diazoamino-azo-benzene or 1-(4-nitrophenyl)-3-(4-phenylazo phenyl)triazene.

11. The method of claim 10 wherein the reagent further comprises an inert filler.

12. A device for testing for a substance on a surface wherein the substance is lead or cadmium comprising:
   a cartridge;

two compartments within said cartridge wherein one compartment contains a reagent that reacts with the substance and the other compartment contains an activating solution; and an absorbent ball of material mounted at one end of the cartridge, wherein the reagent and activating solution are combined and mixed within the cartridge before the device is used.

13. The device of claim 12 wherein each of the two compartments is a breakable cartridge.

14. The device of claim 12 wherein one of the compartments is a breakable cartridge.

15. The device of claim 12 wherein the substance is lead.

16. The device of claim 15 wherein the reagent includes a rhodizonate dye.

17. The device of claim 15 wherein the activating solution is a buffer having a pH of between about 2 and about 3.

18. The device of claim 12 wherein the substance is cadmium.

19. The device of claim 18 wherein the reagent includes 4-nitronaphthalene-diazoamino-azo-benzene or 1-(4-nitrophenyl)-3-(4-phenylazophenyl)triazene.

20. A method for testing for cadmium on a surface comprising:
soaking a filter paper with an activator solution,
wetting the filter paper with water,
placing the filter paper on a surface,
placing drops of 4-nitronaphthalene-diazoamino-azo-benzene or 1-(4-nitrophenyl)-3-(4-phenylazophenyl)triazene on the filter paper, and
detecting the presence of cadmium by inspecting the filter paper for a pink color.

* * * * *

UNITED STATES PATENT AND TRADEMARK OFFICE
CERTIFICATE OF CORRECTION

PATENT NO. : 5,039,618

DATED : August 13, 1991

INVENTOR(S) : Stone

It is certified that error appears in the above-identified patent and that said Letters Patent is hereby corrected as shown below:

On the title page, item [21] Appl. No.: please change "449,488" to --499,488--.

Signed and Sealed this

Twentieth Day of October, 1992

Attest:

DOUGLAS B. COMER

*Attesting Officer*         Acting Commissioner of Patents and Trademarks